United States Patent
Schwery et al.

(10) Patent No.: US 12,070,235 B2
(45) Date of Patent: Aug. 27, 2024

(54) DEVICE AND METHOD FOR PERFORATING A DENSE BONE LAYER

(71) Applicant: BOSONIC AG, Bern (CH)

(72) Inventors: Andrè Schwery, Rombach (CH); Jörg Mayer, Niederlenz (CH)

(73) Assignee: BOSONIC AG, Bern (CH)

( * ) Notice: Subject to any disclaimer, the term of this patent is extended or adjusted under 35 U.S.C. 154(b) by 596 days.

(21) Appl. No.: 17/257,053

(22) PCT Filed: Jul. 2, 2019

(86) PCT No.: PCT/EP2019/067749
§ 371 (c)(1),
(2) Date: Dec. 30, 2020

(87) PCT Pub. No.: WO2020/007865
PCT Pub. Date: Jan. 9, 2020

(65) Prior Publication Data
US 2021/0177438 A1    Jun. 17, 2021

(30) Foreign Application Priority Data
Jul. 3, 2018 (CH) .................................. 00834/18

(51) Int. Cl.
*A61B 17/16* (2006.01)
*A61B 17/32* (2006.01)
(Continued)

(52) U.S. Cl.
CPC ...... *A61B 17/1637* (2013.01); *A61B 17/1604* (2013.01); *A61B 17/32002* (2013.01);
(Continued)

(58) Field of Classification Search
CPC ............ A61B 17/1637; A61B 17/1604; A61B 17/320002; A61B 17/32053;
(Continued)

(56) References Cited

U.S. PATENT DOCUMENTS 4,571,183 A     2/1986  Nash
4,838,853 A *   6/1989  Parisi ............. A61B 17/320016
                                                    601/2
(Continued)

FOREIGN PATENT DOCUMENTS

EP      1 698 285      9/2006
JP      2-74014 U      6/1990
(Continued)

*Primary Examiner* — Kevin T Truong
*Assistant Examiner* — Diana Jones
(74) *Attorney, Agent, or Firm* — Rankin, Hill & Clark LLP

(57) ABSTRACT

A device and method for perforating a dense bone layer. The device includes a vibration generator for generating mechanical vibration, in particular ultrasonic vibration, and an instrument with an elongated shaft and a distal end piece including a perforator. The distal end piece is arranged at a distal end of the shaft and the proximal end of the shaft is connected or connectable to the vibration generator. The perforator has the form of a solid or a hollow cylinder. The vibration generator, the shaft and the distal end piece are adapted to each other for the shaft to transmit, when connected to the activated vibration generator, mechanical vibration from the vibration generator to the distal end piece and for vibrating the perforator in a direction parallel to its cylinder axis.

28 Claims, 11 Drawing Sheets

(51) Int. Cl.
*A61B 17/3205* (2006.01)
*A61B 17/34* (2006.01)
*A61B 90/00* (2016.01)
*A61D 1/00* (2006.01)

(52) U.S. Cl.
CPC .... *A61B 17/32053* (2013.01); *A61B 17/3421* (2013.01); *A61B 17/1671* (2013.01); *A61B 2017/320064* (2013.01); *A61B 2017/32007* (2017.08); *A61B 2017/320072* (2013.01); *A61B 2017/320098* (2017.08); *A61B 2017/3454* (2013.01); *A61B 2090/036* (2016.02); *A61D 1/00* (2013.01)

(58) Field of Classification Search
CPC .......... A61B 17/3421; A61B 2090/036; A61B 2017/32007; A61B 2017/320098; A61B 17/1671; A61B 2017/320064; A61B 2017/320072; A61B 2017/3454; A61D 1/00

See application file for complete search history.

(56) References Cited

U.S. PATENT DOCUMENTS

| | | | |
|---|---|---|---|
| 4,895,146 A * | 1/1990 | Draenert | A61F 2/4644 606/180 |
| 5,938,633 A * | 8/1999 | Beaupre | A61B 17/320068 604/22 |
| 6,551,337 B1 | 4/2003 | Rabiner et al. | |
| 8,409,230 B2 | 4/2013 | Pamichev et al. | |
| 9,072,528 B2 | 7/2015 | Cournoyer et al. | |
| 9,237,894 B2 | 1/2016 | Hernandez et al. | |
| 2004/0127925 A1 * | 7/2004 | Du | A61B 17/32053 606/167 |
| 2008/0234711 A1 | 9/2008 | Houser et al. | |
| 2009/0221940 A1 * | 9/2009 | Marlinghaus | A61B 17/225 601/4 |
| 2010/0130867 A1 | 5/2010 | Vercellotti et al. | |
| 2010/0191173 A1 | 7/2010 | Kimura et al. | |
| 2013/0190764 A1 | 7/2013 | Lesinski et al. | |
| 2015/0216551 A1 * | 8/2015 | Dieras | A61B 17/320068 606/169 |
| 2015/0230823 A1 * | 8/2015 | Morgan | A61B 17/3476 604/272 |
| 2015/0265287 A1 | 9/2015 | Berberich | |
| 2016/0089208 A1 | 3/2016 | Vetter | |
| 2016/0128708 A1 * | 5/2016 | Mikus | A61B 17/22004 606/110 |
| 2017/0172611 A1 * | 6/2017 | Tanigami | A61B 17/1682 |
| 2017/0273707 A1 | 9/2017 | Sakamoto et al. | |

FOREIGN PATENT DOCUMENTS

| | | |
|---|---|---|
| JP | 2010-252839 A | 7/2010 |
| JP | 2012-65839 A | 4/2012 |
| JP | 2015-510410 A | 4/2015 |
| WO | 2007/101362 | 9/2007 |
| WO | 2014/150193 | 9/2014 |
| WO | 2015/045438 A1 | 4/2015 |
| WO | 2015/179646 | 11/2015 |
| WO | 2016/057576 | 4/2016 |
| WO | 2017/073970 | 5/2017 |

* cited by examiner

DEVICE AND METHOD FOR PERFORATING A DENSE BONE LAYER

BACKGROUND OF THE INVENTION

Field of the Invention

The invention resides in the field of medical technology and regards a device suitable for perforating a dense bone layer with the aim of enabling transport of blood, oxygen and/or viable cells through the dense bone layer from trabecular bone tissue and/or bone marrow on an inner side of the dense bone layer to a repair site on an opposite, outer side of the dense bone layer, and for therewith enhancing tissue repair or tissue regeneration and tissue growth in the repair site. The invention also relates to a method for perforating a dense bone layer with the aid of the named device.

Description of Related Art

Methods in the field of the invention are known as marrow-stimulation and include microdrilling or microfracturing the dense bone layer situated between vascularized trabecular bone and/or bone marrow (inner side of the dense bone layer) and a tissue layer in need of tissue repair, tissue regeneration or tissue growth to compensate tissue loss due to injury, illness, degeneration or surgical intervention, or to augment tissue (outer side of the dense bone layer). The dense bone layer to be perforated is in particular a subchondral bone plate in a joint of a human or animal patient. The subchondral plate is perforated for enhancing cartilage repair or growth of cartilage or suitable repair tissue (e.g. vascularized granulation tissue or fibrous or fibrocartilaginous tissue), or for growth of bone tissue or ossification of cartilage tissue for fusion of a suitably prepared and stabilized joint (arthrodesis).

The known process of microdrilling usually includes producing with the aid of a rotating drill bit a plurality of bores through the dense bone layer, the bores having a diameter of, e.g., 0.5 to 2 mm, and, depending on the thickness of the dense bone layer, a depth in the range of e.g. 2 to 10 mm. The known process of microfracturing includes producing openings in the dense bone layer by impacting a usually conical awl into the dense bone layer with the aim of not only producing an opening in the dense bone layer but, in particular, of producing microfractures in the bone tissue surrounding this opening, wherein these microfractures are thought to complement perforation of the dense bone layer, and therefore the openings produced by microfracturing usually have a rather smaller depth than the openings produced by microdrilling. The advantage of the microdrilling process is the fact that debris are easily removed from the bore along the grooves of the drill bit and therefore do not obstruct blood flow through the produced bore; its disadvantage is the inevitable thermal load on the bone tissue and the possibly non-negligible mechanical weakening of the dense bone plate. The advantages of the microfracturing process are its simplicity, the possibly smaller opening depth, and the fact that substantially no debris remains in the opening leaving the latter unobstructed; its disadvantages are the compaction of the bone tissue adjoining the opening (damage to and sealing of trabecular bone structure), the friction between the bone tissue and the tool, and in particular the dependence of the achievable microfracturing on the usually not very well known quality of the bone tissue at hand, which renders the perforation quality and the mechanical weakening of the dense bone plate hardly predictable.

Known instruments for microdrilling and microfracturing usually include a shaft with a distal end portion designed as drill bit for microdrilling or designed as conical prick for microfracturing. Depending on the site and the method in which microdrilling or microfracturing is to be performed, the approach for such instruments is substantially perpendicular to the dense bone layer, i.e. in the same direction, in which the dense bone layer is to be perforated ("direct" approach). This approach is in particular possible in open joint surgery and for similar surgical methods. More often however, and in particular for minimally invasive joint surgery, the approach is substantially parallel to the dense bone layer to be perforated, i.e. substantially angled relative to the perforation to be produced ("indirect" approach). Instruments suitable for the direct approach may include a substantially straight shaft with a coaxially arranged distal end portion. Instruments suitable for the indirect approach need to be angled, curved or otherwise adapted such that the principal direction in which the distal end portion acts on the dense bone layer is non-parallel with the principal axis of the shaft.

The following shortly commented publications constitute background for the present invention, wherein:

EP1698285 discloses a straight instrument for microfracturing a subchondral bone plate, e.g., during open joint surgery, the tool including a distal end portion equipped with a plurality of conical pricks to be impacted into the dense bone layer for simultaneous creation of a plurality of openings.

U.S. Pat. No. 9,237,894, WO2014/150193 and WO2015/179646 disclose angled awl-shaped instruments suitable for microfracturing subchondral bone in an indirect approach.

U.S. Pat. No. 9,072,528 discloses a microfracturing instrument which includes, on two opposite lateral sides of its distal end portion, bent conical pricks, the tool being suitable for the indirect approach when driven in oscillating rotation around its longitudinal axis.

WO2017/073970 discloses a microfracturing instrument suitable for arthroscopic surgery (indirect approach) and including a tube-shaped distal end with a cutting edge suitable for punching through the dense bone layer, the tube shaped distal end being arranged on the shaft at an angle.

U.S. Pat. No. 8,409,230 discloses a variety of microfracturing or microdrilling instruments which all include a shaft and a distal end piece arranged at an angle to each other, the distal end piece not being rigidly connected with the shaft but arranged for combined operation (shaft impacting or rotating the distal end piece), wherein impaction may be driven or assisted by ultrasonic energy.

US 2004/0127925 describes percutaneous surgical instruments for de-bulking calculi or drilling bone including actuators for generating vibrations at ultrasonic frequencies and a horn for amplifying the actuator vibrations. A fixed probe is used for disintegrating calculi, which may be aspirated through a lumen through the fixed probe and the horn.

WO2016/057576 discloses an instrument including a shaft carrying at its distal end a conical prick for microfracturing or a ring curette for scraping the bone layer, prick and curette having an axis perpendicular to the shaft. The proximal end of the shaft is connected to an ultrasound generator, wherein the generator is adapted to the instrument for longitudinal vibration of the shaft and therewith vibration of the prick or curette parallel to the shaft axis, i.e., in operation, substantially parallel to the surface of the dense bone layer.

SUMMARY OF THE INVENTION

It is the object of the present invention to improve the above shortly described known devices and methods for perforating a dense bone layer without rendering device and method more involved. With the aid of device and method according to the invention it is to be possible to produce accurately defined openings (as with microdrilling) of a sufficient depth for the stated aim, wherein creation of these openings is to leave a substantial part of the bone tissue adjoining the opening unaffected (substantially no thermal damage, nor tissue compaction, nor uncontrolled fracturing) and to leave the opening free of bone debris.

This object is achieved by device and method according to the invention. Important in microfracturing is that on is able to penetrate through the dense subchondral bone layer into the trabecular bone and not just into the interface—in the knee this means, for example, that the cannula penetrates 7-8 mm into the bone—the object is to create access to the trabecular bone marrow and leave this open as long as possible in a small defect being attraumatic as possible. Therefore cauterizing effects by the instrument should be minimized (minimization of heat).

The device according to the invention includes a perforation instrument with a shaft and a distal end piece, and it further includes a vibration generator, preferably a generator of ultrasonic vibration, e.g. a piezoelectric vibration generator. The distal end piece is arranged at the distal end of the shaft and it includes a solid (non-hollow) or a hollow, substantially cylindrical perforator, which, for the perforation process, is impacted into or through the dense bone layer. The distal end piece may be constituted by the perforator alone or may include further elements, e.g., coupling elements for coupling the perforator to the shaft. The cylinder axis of the perforator (principal perforator axis) is parallel or angled relative to a principal longitudinal shaft axis. The proximal end of the shaft is directly or indirectly connected or connectable to the vibration generator. The vibration generator, the shaft and the distal end piece are adapted to each other such that a principal vibration direction of the perforator is oriented parallel to the cylinder axis of the latter or parallel to the impaction direction respectively. The device according to the invention may further include a cutting tube as part of the perforator. The cutting tube may an integral part of the perforator and forms preferably the distal end of the perforator. The cutting tube may also be coupled, in particular rigidly coupled, to the distal end of the perforator. The cutting tube may be coupled to the perforator in a way that the principal perforator axis (B) and the principal cutting tube axis coincide or are parallel to each other. Another embodiment of the invention refers to a device, wherein the principal perforator axis (B) and the principal cutting tube axis build an angle. It is preferred that the angle is >90° and <180° and is particularly preferred between 120° and 150°. The perforator including a cutting tube may have an oblique-cut distal end.

The term "proximal" as used herein refers to the nearest to the point of attachment to the housing of an ultrasonic surgical instrument or respectively to the user of that instrument. The term "distal" as used herein refers to being situated away from the point of attachment to the housing of an ultrasonic surgical instrument or respectively to the user of that instrument. The distal edge is used to punch or cut the bone.

Using the method according to the invention, the distal face of the perforator is positioned and held against the dense bone layer and is impacted into the latter by the effect of being vibrated in the impaction direction and possibly, in addition, by being urged against the dense bone layer. On impaction, a solid perforator will compact the bone tissue from the opening being created at the bottom of this opening and a hollow perforator will take up bone tissue in its inside to be removed from the created cylindrical opening through the hollow perforator or stored within the perforator and removed together with the perforator. Due to the combination of a cylindrical perforator being vibrated in impaction direction, which prevents at least lateral bone compaction, and which reduces lateral friction between perforator and bone tissue, the opening such created may be substantially cylindrical and at least its lateral walls are constituted by uncompromised and therefore fully viable bone tissue, and, as bone tissue from the inside of the opening is left compacted at the bottom of the opening or is removed "automatically", the opening remains unobstructed in any case, without necessitating a further method or control step. In case that the perforator of the inventive device is hollow it is even possible to introduce ring-shaped openings (openings in form of a cylinder barrel) within the bone, where a bone core is left (cf. FIG. 24). This method allows to increase the surface for bleeding despite the same number of perforations. Nevertheless it is important not to destroy the bone core, neither by fracturing nor by heat. In addition, the device has to be designed in a way to break off the bone core from the underlying bone tissue, such as trabecular bone, without damage of the bone core.

Compared with the known method of microfracturing, the effect of the method according to the invention is better predictable regarding achievable flow through the perforation and regarding mechanical weakening of the dense bone layer and therewith allows better optimization, i.e. better achievement of optimum flow at minimum mechanical weakening.

Preferable diameters of the cylindrical openings to be created with device and method according to the invention are similar to the openings produced with known such devices and methods, i.e., they are in the range of e.g. 0.5 to 2 mm. Preferable diameters of the ring-shaped openings to be created with device and method according to the invention are larger than the cylindrical openings, i.e. they are in the range of e.g. 1.5 to 3 mm, wherein the width of the gap between bone core and surrounding bone may between 0.1 and 0.5 mm. The depth of the openings is dependent on the dense bone layer to be perforated and is, e.g., for the subchondral bone plate in a knee of an adult human patient in the range of 5 and 8 mm. In the smaller ankle joint, opening diameter and depth will be smaller. Preferably a plurality of openings is produced, wherein for the above example of a human knee joint, a distance between neighboring openings is, e.g., in the range of between 5 and 10 mm.

Preferably, the shaft and the distal end piece (including the perforator) of the device according to the invention are rigidly coupled to each other or form together one single piece, wherein the shaft is designed to transmit the vibration energy as fully as possible from its proximal end to the distal end piece or the perforator respectively. However, it is possible also that shaft and distal end piece are designed as two separate or only loosely connected pieces such that the vibrating shaft acts in the way of a hammer on the distal end portion or the perforator respectively (transmitting only the forward directed half of the vibration).

Preferably, the material of the shaft and the perforator of the device according to the invention is a metallic material, such as, e.g., stainless steel or titanium. Preferably, the connection between the shaft and the vibration generator is releasable and the instrument including the shaft and the distal end piece is disposable.

The device according to the invention is, e.g., a hand-held device wherein a handle portion thereof houses the vibration generator being supplied with the necessary energy by a battery or through a corresponding cable connecting the hand piece to a control and supply unit. The preferred frequency for the vibration is in the ultrasonic range, preferably in the range 15 and 40 kHz or between 20 and 30 kHz and of an energy sufficient for achieving an amplitude in the micrometer range for the distal end of the perforator, between 20 and 120 µm or preferably between 60 and 100 µm.

For achieving a vibration parallel to a perforator axis for a perforator being rigidly fixed to the shaft and with a perforator axis substantially coinciding with the shaft axis, the vibrating system of generator, shaft and perforator is designed and activated to vibrate in a standing wave mainly longitudinally and with an anti-node position at the distal end of the perforator. If the perforator is rigidly connected to the shaft at an angle (perforator axis or impaction direction non-parallel to principal shaft axis) the same is achieved by designing and activating the vibrating system of vibration generator, shaft and perforator to vibrate in a flexural mode with an anti-node position at the distal end of the shaft or by connecting the distal end piece to a mainly longitudinally vibrating shaft at a node position of the latter. The same (redirection of vibration direction from parallel to the shaft axis to parallel to the perforator axis) can be achieved by corresponding design of the distal end piece and its connection to the shaft, e.g. as disclosed in the publication WO2007/101362. If the perforator is only loosely or not attached to the shaft, the anti-node position is to be situated at the distal end of the shaft.

The present invention refers to a device, wherein the shaft and the distal end piece with the perforator are loosely connected or separate and are arranged for the distal end of the shaft to be able to hammer against the perforator. Another embodiment of the invention refers to a device, wherein the principal shaft axis and the principal perforator axis (B) coincide or are parallel to each other. Another embodiment of the invention refers to a device, wherein the shaft is designed to vibrate in a longitudinal mode.

When perforating bone there are several possibilities to dispose the removed bone fragments. One possibility is to impact the cut dense bone core into the underlying trabecular bone (cf. FIG. 15), which is compacted so that the bleeding can be impaired. The fragments may further be aspirated by special devices or the devices used for perforation. This often results in obstruction of the aspirating device. Using the devices according to the present invention the bone may be removed as one bone core or fragment and not as debris. This bone core may remain within the distal end of the perforator or the cutting tube. In the following the bone core may either be removed to the outside and flush away from the operation side together with the blood, etc., or it may be sucked further into a space of the shaft or the perforator and stored until all perforations are made and the instrument will be removed from the operation side. In this case the perforator may be a disposable article which is removed from the device and through away after each surgery together with the extracted bone particles. This makes a laborious cleaning of the device redundant. There is no bone debris that may obstruct a liquid supply or a suction device and has to be pushed away.

One objective of the invention is to provide a device suitable to reduce the blockage by bone debris within the instrument. The invention refers therefore to a device, wherein the perforator or the shaft includes an opening suitable for storage of removed bone fragments. Another embodiment of the invention refers to a device, wherein the shaft or the perforator includes a pipeline suitable for liquid supply to the opening or applying vacuum to the opening. Using the liquid supply it is possible to remove the bone core from the cutting tube or the perforator and the vacuum is suitable to support retaining the bone core within the opening.

There may be specific elements located interior of the perforator or its cutting tube that facilitates the breakage of the bone core after cutting into the dense bone. Such elements may be ribs. Cross-threading of the ribs exert force to the bone core removing it from the underlying layers of the bone tissue. Consequently, another aspect of the invention refers to a device, wherein the perforator or the cutting tube includes protruding elements, such as ribs, on the inner surface suitable to exert torsion force to the cut bone. It may also be useful to shred the bone cores after being removed. Therefore the perforator or the cutting edge may have slicing elements within the interior.

The perforator may have e.g. a circular, an oval, or regularly or irregularly polygonal cross section. A solid perforator preferably further includes a pointed tip, i.e. it has the form of an awl, wherein the largest cross section of the tip is the same or slightly larger than the cross section of the cylinder. The perforator may also have the form of a blade or chisel (narrow elongated cross section) and include a distal edge. A hollow perforator has the form of a bone punch having a distal edge. Therein, edges of the perforator, which, in operation, are in narrow contact with the bone tissue are preferably sharp or serrated, i.e. include a saw-like structure of a size in the visible or sub-visible range. This is in particular applicable for distal edges of blade-, chisel-, and punch-shaped perforators, but may also be applicable for lateral edges of any perforator having a polygonal cross section and for the edges of a pyramid-shaped tip of a solid perforator.

One preferred embodiment of the invention refers to a device, wherein the perforator or its cutting tube is a hollow cylinder and includes a distal edge. This distal edge is preferably formed as a sharp cutting end suitable to cut dense bone. Therefore one embodiment refers to a device according, wherein the distal edge terminates an inner and/or outer tapering of a cylinder wall. It is further preferred that the distal edge includes a groove at the inner or outer side. The groove may represent a depression in the lateral wall of the perforator or its cutting tube. The width of said groove may be 0.3 to 1.5 mm. The groove around may have a constant or unvaried thickness. It is preferred that the transition of the groove to the distal edge or the groove is smooth. Therefore it is preferred that the transition between the groove and the surface of the edge is continuously or in form of a curvature. In case that the transition is curved, it is possible to create a defined but stable cutting edge. Alternatively, there may be a step near the distal edge where the thickness of the lateral wall increases towards the distal end.

The sharp cutting edge may also be formed by a separate element attached to the distal end of the perforator or its cutting tube. Such an element may be a ring, e.g., made of a ceramic material, the same material or another alloy than the perforator, clamped into the opening of the hollow perforator or the hollow cutting tube. The ring may also be welded to the perforator or the cutting tube after being put onto the distal end thereof. It is also possible to form a sharp cutting edge by cutting into the lateral wall of the perforator or its cutting tube and bend or fold the resulting parts alternatingly outwards and inwards.

The device according to the invention may further include a cannula or a guide shaft around the shaft of the perforation instrument. Thereby transmission of vibrational energy though the instrument shaft is to be as efficient as possible and friction between the shaft and the cannula as low as possible. This can be achieved by providing, in an axial position in which the most distal node position of the shaft is situated, a region in which radial clearance between instrument and cannula is at a minimum. This is realized by the shaft comprising, at least in the most distal node position an increased cross section, and by the through opening of the guide shaft portion extending form the distal end portion to beyond the most distal node position of the sonotrode including a constant cross section. The shaft may further include portions of a larger cross section at other node positions. In addition also the cannula may have regions of larger cross sections at one or more node positions. It is further preferred that the arrangement including shaft and cannula has polymeric sliding surfaces to minimize friction loss. These surfaces may be formed by a polymeric ring around the distal end of the shaft or the perforator, respectively its cutting tube. The polymeric ring may be made of PEEK. Alternatively, there may be a polymeric bushing attached at the inner surface of the cannula, which can also be made of PEEK. Consequently, the region o larger cross section may be formed as polymeric attachment to the cannula or the shaft. The region of larger cross section may also have a polymeric coating.

BRIEF DESCRIPTION OF THE DRAWINGS

Exemplary embodiments of device and method according to the invention are described in further detail in connection with the appended FIGS., wherein.

DESCRIPTION OF THE PREFERRED EMBODIMENTS

Figure 1:
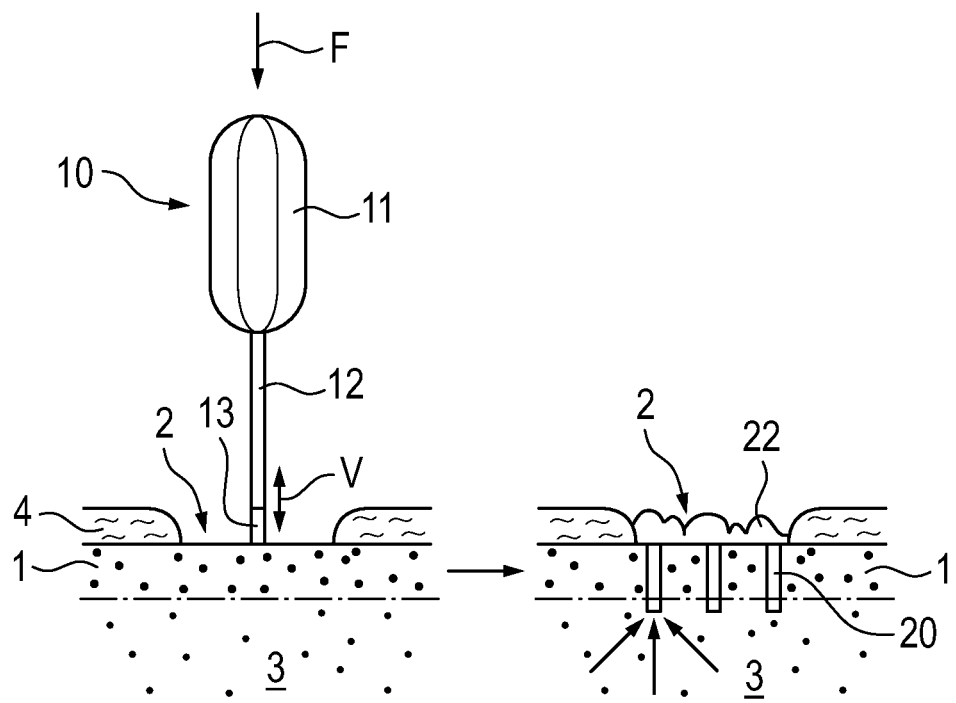
FIGS. 1 and 2 illustrate the direct and the indirect approach for perforation of a dense bone layer using a device according to the invention.

In all appended FIGS., same reference numerals designate same elements or similar elements serving same functions.

FIG. 1 illustrates in a very schematic manner, the direct approach for perforating a dense bone layer 1 using a device 10 according to the invention, wherein the left hand side of FIG. 1 shows the device 10 positioned for the perforation process, and the right hand side shows the perforated dense bone layer and illustrates the desired flow of blood, oxygen and/or cells through the perforation. As already mentioned further above, the dense bone layer is situated between a repair site 2 (outer side of the dense bone layer) and a region 3 or layer of trabecular bone and/or bone marrow (inner side of bone layer), wherein there is usually a gradual transition between dense and trabecular bone tissue and not, as illustrated, a sharp line separating the two. The dense bone layer 1 is, e.g., a subchondral bone plate and the repair site 2 is a location, in which cartilage 4 covering the subchondral bone plate 1 is missing or in need of repair, strengthening, augmentation or possibly ossification. The perforation process is e.g. a part of an open surgery on a human or animal patient.

The device 10 as illustrated in FIG. 1 has the form of an ultrasonic hand piece and includes a handle 11 housing the vibration generator (not shown), a shaft 12 coupled to the vibration generator and a substantially cylindrical perforator 13 coupled to the distal end of the shaft 12 in a substantially coaxial manner. For the perforation process, the distal face of the perforator 13 is positioned and held against the outer surface of the dense bone layer 1 (arrow F), such that the principal perforator axis forms an angle of, e.g., about 90° with the bone surface. Furthermore, the vibration generator is activated to vibrate (double arrow V) the perforator 13, and the device is possibly urged against the dense bone layer 1 (direction of arrow F), therewith driving the perforator 13 into and preferably through the dense bone layer 1 to form an opening 20 from which the perforator 13 is then removed. Preferably, as shown on the right hand side of FIG. 1, a plurality of openings 20 is created. As soon as the perforator 13 is removed from the opening 20, fluid material is flowing from the inner side of the dense bone layer 1 to its outer side as shown with small arrows, in particular blood carrying oxygen and cells, forming, on the outer side of the dense bone layer 1, a blood clot 22, which enables and/or enhances tissue growth or tissue repair in the repair site 2.

Figure 2:
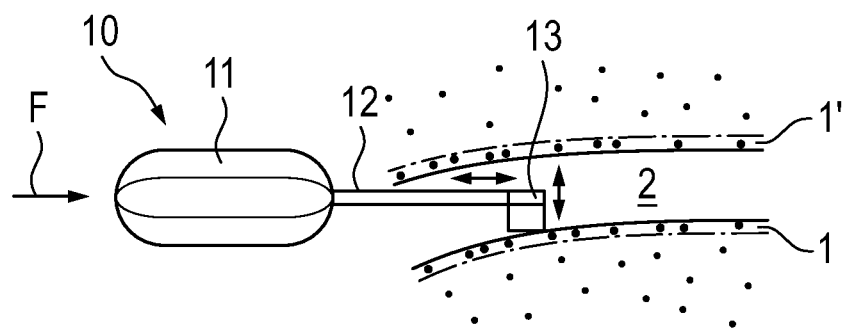

FIG. 2 illustrates, in the same schematic manner as FIG. 1, the indirect approach for perforating a dense bone layer 1 using a device according to the invention. For this perforation process, the perforator 13 is coupled at an angle to the distal end of the shaft 12 and is positioned against the dense bone layer 1 by approaching the device 10 in a direction as indicated with arrow F, i.e. substantially parallel to the dense bone layer 1. The perforation process as illustrated in FIG. 2 is e.g. part of a minimally invasive surgical operation on a joint of a human or animal patient, wherein the dense bone layer to be perforated is one of a pair of subchondral bone plates (1 and 1') situated opposite each other in the joint. In another, exemplary application of the process as illustrated in FIG. 2, the dense bone layer 1 to be perforated is the cortical bone layer of one of a pair of neighboring vertebrae facing the intervertebral space, from which the intervertebral disc and possibly also the cartilage tissue covering the subchondral bone plates has been partly or fully removed.

Figure 3:
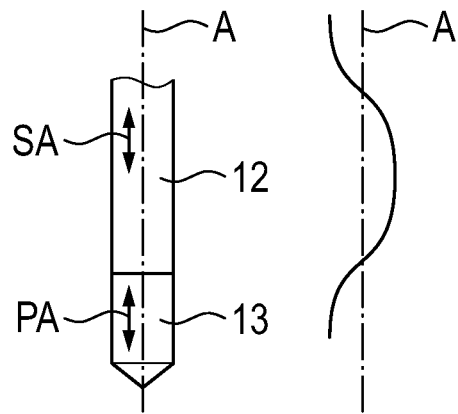
FIGS. 3 to 8 show exemplary embodiments of arrangements of shaft and perforator suitable for the device according to the invention.
Figure 4:
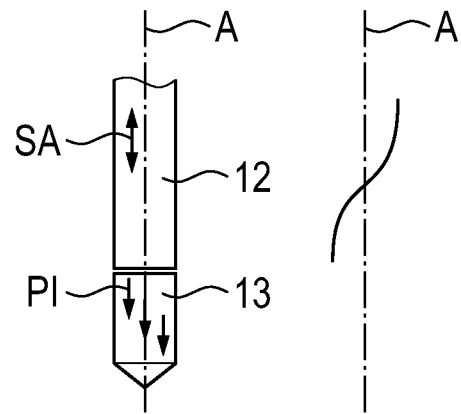
Figure 5:
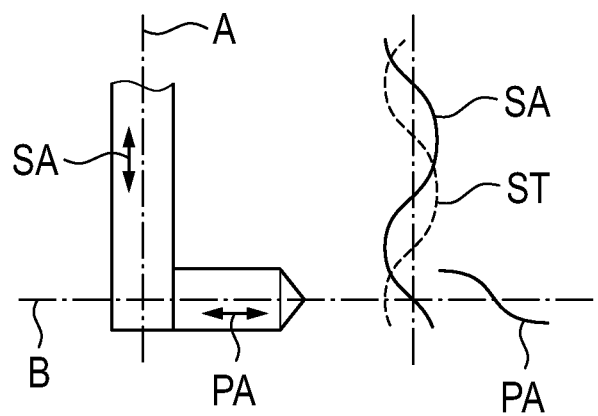

FIGS. 3 to 8 illustrate various embodiments of instruments suitable for the device according to the invention and including a shaft 12 and a distal end piece with a perforator 13, wherein only a distal portion of the shaft 12 is shown. For further illustrating the desired vibration mode of the instruments, FIGS. 3 to 5 show on their right hand side corresponding schemata. In all FIGS. 3 to 8, the perforator 13 has the form of a cylinder with a tapering tip as further illustrated in FIG. 9. However, all further embodiments of perforators as illustrated in the following FIGS. 10 to 14 are also applicable for the instruments as illustrated in FIGS. 3 to 8. In particular, the perforator may have the form of a prism.

The instrument according to FIG. 3 includes a perforator 13 and a shaft 12, the shaft having at least in its distal end region substantially the same cross section as the perforator 13. Shaft 12 and perforator 13 are made as one piece or as two rigidly coupled pieces having one common principal axis A, rendering the instrument suitable for the direct approach according to FIG. 1. Shaft 12 and perforator 13 are designed to vibrate principally longitudinally (double arrows SA and PA) in a standing wave having an anti-node position in the region of the distal end of the perforator 13, as indicated in the vibration scheme on the right hand side of the figure.

The instrument shown in FIG. 4 is similar to the instrument of FIG. 3 but the perforator 13 is only loosely or not coupled to the shaft 12. Therein the shaft 12 is designed and activated to vibrate mainly longitudinally (double arrow SA) in a standing wave having an anti-node position at the distal face of the shaft, wherein only the distally directed half wave is transmitted to the perforator 13 resulting in a series of intermittent blows to the latter (arrows PI).

Both instruments illustrated in FIGS. 3 and 4 may be further equipped for creation of openings with a limited depth. Elements for such depth limitation may include full or partial collars extending at a corresponding axial distance from the distal face of the perforator radially from the perforator 13 or from the distal shaft end region (see also FIG. 10). In the embodiment according to FIG. 4, an outer ring of the distal face of shaft 12 may serve as depth limiting element, if the shaft 12 has a correspondingly larger cross section than the perforator 13.

Figure 6:
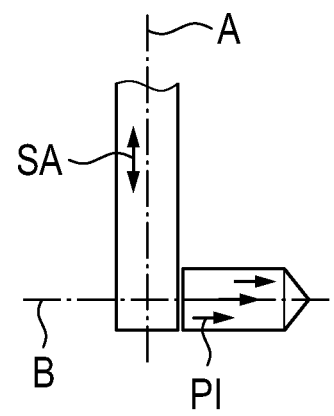

FIGS. 5 and 6 illustrate an instrument suitable for the device according to the invention and including a shaft 12 and distal end piece with a perforator 13, the instrument being suitable for the indirect approach (FIG. 2). The perforator 13 is arranged relative to the shaft 12 for the principal shaft axis A to not coincide with the principal perforator axis B but to form an angle therewith, as illustrated e.g. an angle of 90°, and the perforator 13 is rigidly coupled to the shaft 12 (FIG. 5) or is loosely coupled or not coupled (FIG. 6) thereto. The shaft 12 is designed and activated for vibrating principally or in addition to the longitudinal or axial vibration (double arrow SA) in a transvers or bending vibration mode (double arrow ST), the bending vibration ST having node positions in anti-node positions of the axial vibration SA. The shaft location in which the perforator 13 is coupled to the shaft 12 or with which the shaft is acting on the perforator is a node position of the axial shaft vibration (SA), i.e., an anti-node position of its bending vibration (ST), such effecting an axial or longitudinal vibration in the rigidly fixed perforator 13 (double arrow PA, FIG. 5), the perforator 13 being preferably designed for an anti-node position of the named vibration PA in the region of its distal face. In the case of the perforator 13 not being rigidly fixed to the shaft 12 (FIG. 6) the vibration of shaft 12 is only partially transmitted to the perforator 13 in the same manner as discussed in connection with FIG. 4, i.e., the shaft 12 will act on the perforator 13 with a series of intermittent hammer blows (arrows PI).

In a process of perforating a dense bone layer using an instrument as illustrated in FIGS. 5 and 6, the depth of the openings to be created is limited by the shaft 12, i.e., this depth is limited to be at the most as large as the axial length of the perforator 13. However, for limiting the depth of the openings to be created, further depth limiting elements as, e.g., shown in FIG. 10 may be provided on the perforator 13.

Figure 7:
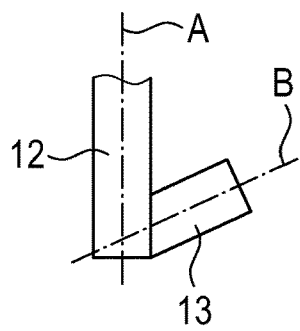
Figure 8:
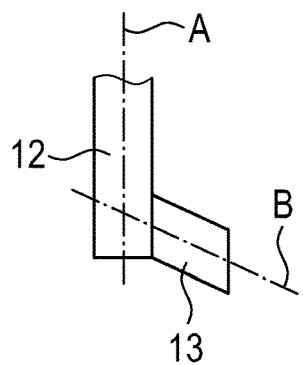

FIGS. 7 and 8 illustrate, very schematically, two further examples of instruments suitable for the device according to the invention, the instruments again including a shaft 12 and a distal end piece with a perforator 13, wherein the principal shaft axis A forms an acute angle (FIG. 7) or an obtuse angle (FIG. 8) with the principal perforator axis B. All comments and explanations in connection with FIGS. 5 and 6 are applicable also for FIGS. 7 and 8.

FIGS. 9 to 13 show exemplary embodiments of perforators 13 suitable for the device according to the invention, all the perforators shown being applicable in any of the instruments as illustrated in FIGS. 3 to 8.

Figure 9:
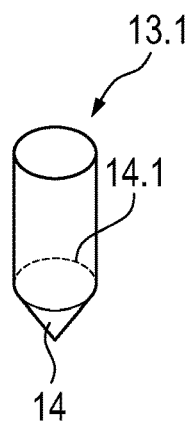
FIGS. 9 to 13 show exemplary embodiments of perforators suitable for the device according to the invention.
Figure 10:
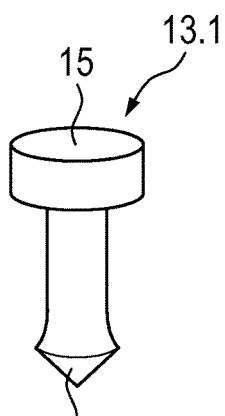

FIGS. 9 and 10 show solid perforators 13.1 including in addition to the cylindrical or prismatic main portion a tapering distal tip 14. If the tip 14 has the form of a pyramid, the edges of this pyramid are preferably sharp or serrated and together with the surface portions between the edges may be plane or concave. Instead of including a tip 14, the distal face of the solid cylinder may have a concave form as indicated in FIG. 9 with a broken line designated with the numeral 14.1, and include a sharp or serrated distal outer edge.

In the perforator according to FIG. 9 the largest (most proximal) cross section of the tip 14 is the same as the cross section of the cylinder portion, but in the perforator according to FIG. 10 it is slightly larger (e.g., by at least 0.1 mm), which results in even further reduction of lateral friction on impaction. In addition, the perforator according to FIG. 10 includes a depth limiting element 15 in form of a step-shaped enlargement of the cross section. Such symmetric or asymmetric depth limiting element can be provided on all perforators shown in FIGS. 9 to 13.

Figure 11:
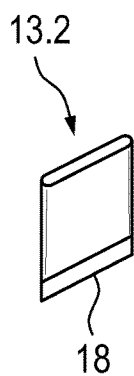
Figure 12:
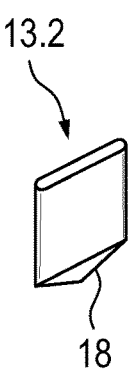

FIGS. 11 and 12 show blade- or chisel-shaped, solid perforators 13.2 having a narrow elongated cross section and a distal edge 18, which may be straight (FIG. 11), or forming a middle point (FIG. 12), but which may also be curved or forming a lateral point.

Figure 13:
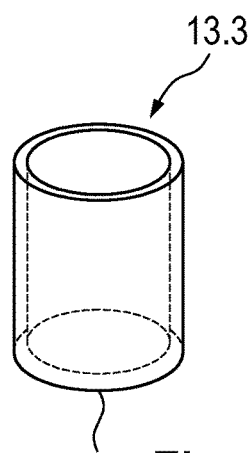

FIG. 13 shows a hollow perforator 13.3 whose distal wall portion is tapering towards a distal edge 18, the taper preferably being restricted to the inside of the hollow cylinder, which, compared with outer tapering results in even less lateral bone compaction. As above mentioned for the solid perforator, a slight reduction of diameter of a main proximal cylinder portion caused by the taper of, e.g., 0.02 to 0.1 mm may help to further reduce lateral friction on impaction.

As mentioned already further above, the perforators as shown in FIGS. 9, 10 and 13 may have circular cross sections as illustrated. However, this is not a condition for the invention. These cross sections may as well be oval, polygonal or of any desired shape.

As also mentioned already further above, the distal edges of the perforators 13.2 and 13.3 as illustrated in FIGS. 11 to 13 are preferably sharp or serrated, the serration being regular or substantially random and having a size in the visible or sub-visible region.

Figure 14:
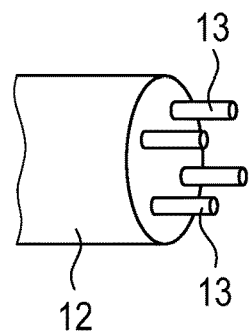
FIG. 14 shows the distal end of a shaft carrying a plurality of perforators.

FIG. 14 shows a further exemplary embodiment of an instrument suitable for the device according to the invention, the instrument including a shaft 12 (only distal end portion shown) carrying at its distal face a plurality of perforators 13, wherein these perforators 13 may, e.g., have the shape of any of the perforators 13.1, 13.2 or 13.3 as illustrated in FIGS. 9 to 13 or described herein. The combination of shaft 12 and a plurality of perforators 13 serves for creating simultaneously a plurality of openings in the dense bone layer, wherein the shaft 12 has a correspondingly larger cross section than each single perforator 13, and wherein the distal shaft face may serve as depth limiting element.

Figure 15:
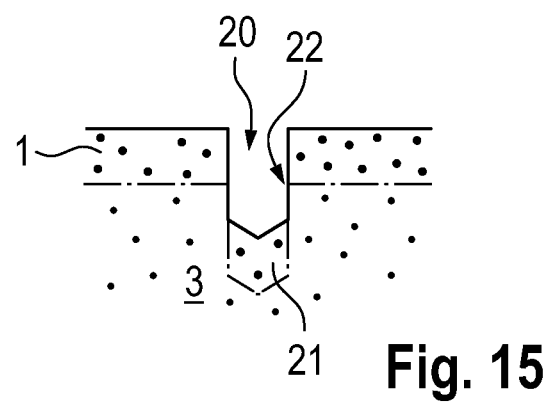
FIG. 15 is an axial section through an opening in a dense bone layer created with a solid perforator.

FIG. 15 shows an opening 20 through a dense bone layer 1, the opening created with the aid of a solid perforator as e.g. shown in FIG. 9 or 10. The opening 20 has, e.g., a depth reaching through the dense bone layer 1 into the trabecular bone tissue 3, wherein bone compaction is found only below the bottom of the opening 20 (region 21 of compacted bone tissue), leaving the lateral walls 22 of the opening fully uncompromised.

Figure 16:
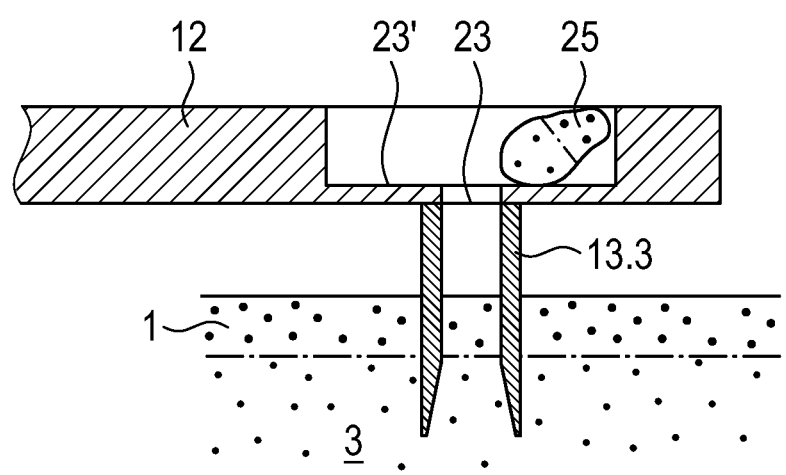
FIG. 16 illustrates creation of an opening in a dense bone layer and removal of bone tissue from the opening with the aid of a hollow perforator.

FIG. 16 is a cross section through the distal portion of an exemplary, angled instrument suitable for the device according to the invention, the instrument including a distal end piece with a hollow perforator 13.3 and a shaft 12, the two being rigidly fixed to each other at an angle of, e.g., 90°. The illustrated instrument is shown in the process of creating an opening through a dense bone layer 1, the distal edge of the perforator 13.3. having reached the trabecular bone tissue 3 beneath the dense bone layer 1.

The instrument as illustrated in FIG. 16 is particularly suitable for creating a series of openings after each other before being removed from the repair site in which the dense bone layer is to be perforated, and for removal of bone tissue from the openings together with the instrument. For this purpose, the shaft 12 includes, in its distal end portion, a transversal through opening 23 being aligned with the channel of the hollow perforator 13.3 and including at least adjacent to the perforator 13.3 a cross section similar to the cross section of the inner perforator channel. This through opening may further include a portion 23' with a larger cross section. Bone debris 25 punched out of a first opening created with the aid of the perforator 13.3 is, e.g., held within the perforator, to be pushed out of the latter into the through opening 23 and 23' of the shaft 12 by bone debris of a second or third opening being created after the first opening. Therein, the vibration of the shaft 12 and the perforator 13.3 facilitates transport of the bone debris through the hollow perforator 13.3.

If the transversal opening 23 through the shaft 12 does not include an enlarged portion as illustrated in FIG. 16, bone debris may be removed from shaft 12 and hollow perforator 13.3 after removal from the repair site using a suitable needle. In a straight instrument as, e.g., illustrated in FIG. 3 including a hollow perforator, the bone debris may be collected in a correspondingly hollow distal end of the shaft and may be removed by disconnecting the perforator from the shaft after removal of the instrument from the repair site. For debris removal it is possible also to provide a lateral opening in the hollow perforator 13.3 through which the debris is pushed and from where it is transported away together with water which, in particular in arthroscopic surgery, is used for continually rinsing the repair site.

Figure 17:
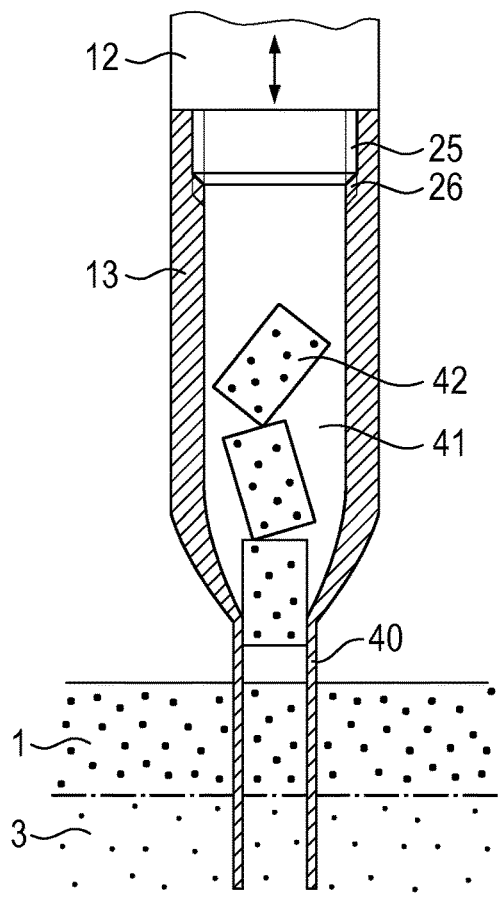
FIGS. 17 and 18 illustrate exemplary embodiments of the arrangement of shaft and perforator suitable for the device according to the invention and suitable for removal of the punched bone cone.
Figure 18:
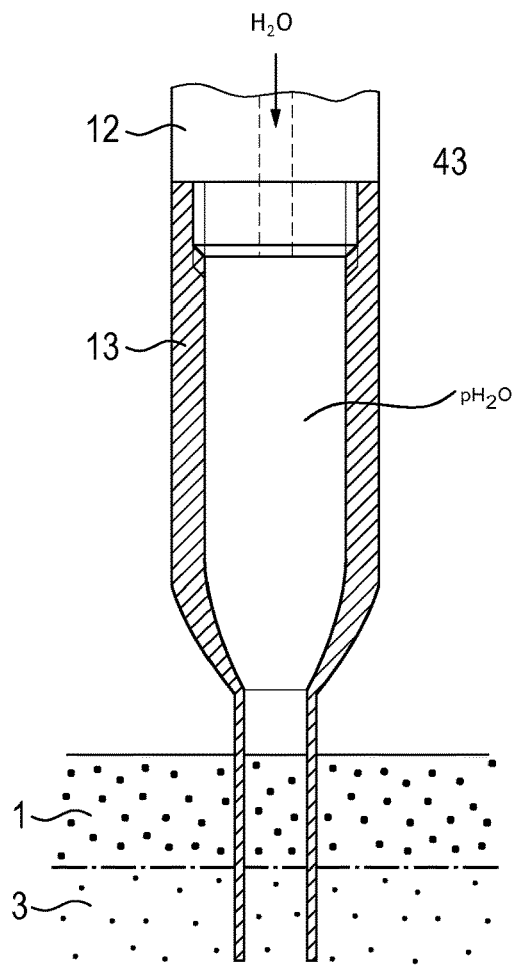

FIGS. 17 and 18 show further exemplified embodiments of an instrument suitable for the device according to the invention. The instruments as shown in FIG. 17 and FIG. 18 are particularly suitable for creating a series of bone openings before being removed from the operation site, and for removal of bone tissue (in particular the complete bone fragments punched out) from the openings created using the instrument. For this purpose, the hollow perforator 13 includes, in its distal end portion, a cutting tube 40. This cutting tube may end in an opening 41 of the perforator having a larger cross section than the cutting tube. Bone fragments 42 punched out of an opening created with the aid of the perforator 13 may be stored within that opening 41. Thus the perforator may include an opening 41 suitable as depot for bone fragments or bone debris. The perforator 13 may be designed as disposable item, suitable to create several bone openings within one operation side and store the resulting (stamped or punched out) bone fragments, After removal from the operation side the bone fragments may be used as sample for tests or as allogenic transplant material. The perforator may through away (with or without the bone fragments) or may easily be cleaned. The embodiment of FIG. 17 is designed so that the vibration of the shaft 12 and the perforator 13 facilitates transport of the bone fragments 42 through the hollow perforator and retain them within the opening 41. The shaft 12 may have a male thread 25 and the perforator a female thread 26 to ensure a proper connection of both elements.

In the embodiment shown in FIG. 18 the bone fragments may further be transported using hydraulic pressure. Therefore, there may be a channel within the shaft 12 suppling a liquid such as water from the handle to the perforator. This liquid flow can be stopped or reversed to generate negative pressure. Alternatively, the liquid may be used to transport (or eject) the bone fragment out of the cutting tube. The bone fragment can be ejected into the operation side and flush away using the liquid generally used to clean the operation side (e.g., from blood). When using this alternative the liquid flow into the perforator is not stopped, but in the moment the perforator cuts into the bone the outflow of the liquid is stopped. Therefore, the pressure within the perforator increases and this pressure can be used to remove the bone fragment from the perforator. In case that a negative pressure is used to transport and store bone fragments punched out, the bone fragments are suctioned. This supports the process of breaking away the portion of the dense bone punched out. Therefore, it is possible to remove the bone within the cutting tube in one piece and without less damage to the surrounding tissue.

The liquid fed through the instrument may further be used to cool the instrument and the perforator, to fill the joint and/or to rinse the operation side. A space between the instrument and a tube or channel (cf. FIGS. 19 to 21) may be used to suck liquid and debris of the bone out of the operational side.

Figure 19:
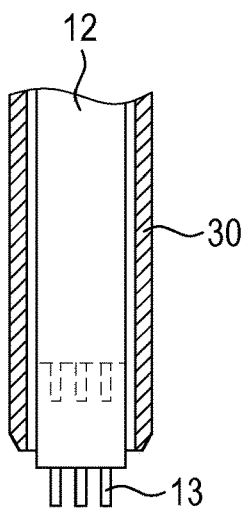
FIGS. 19 to 21 illustrate further exemplary embodiments of the instrument suitable for a device according to the invention, which instruments further include a protective cannula.
Figure 20A:
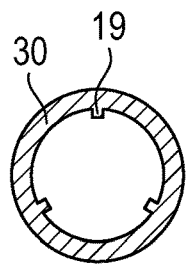
Figure 20A:
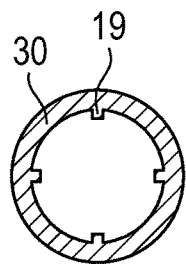
Figure 20B:
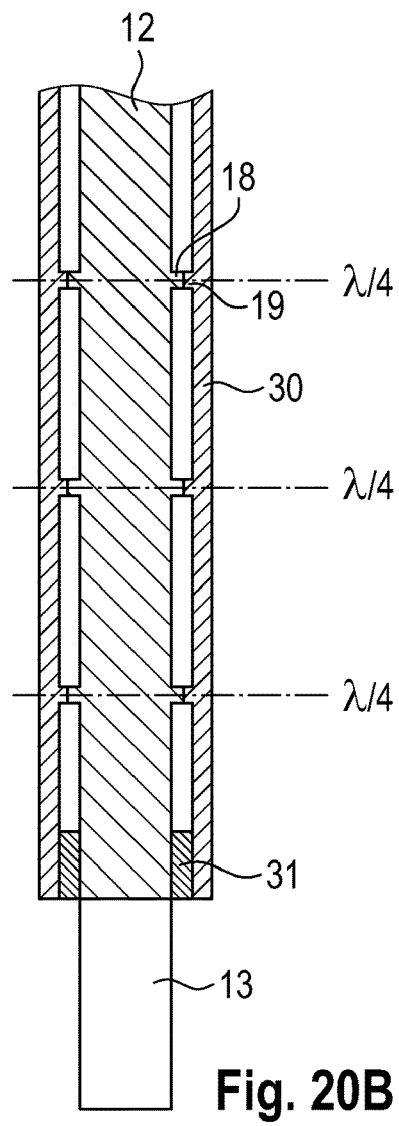
Figure 21:
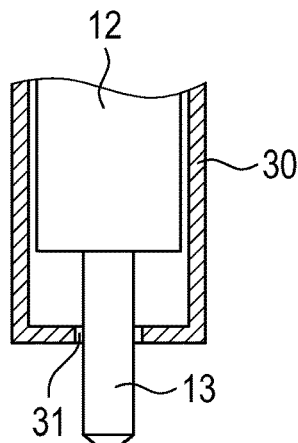

FIGS. 19 to 21 illustrate exemplary embodiments of the device according to the invention which are particularly suitable for arthroscopic or minimally invasive surgery by including a longish and slender shaft 12 situated in a cannula 30, the perforator 13 protruding from the distal end of the cannula and preferably being retractable into the cannula before and after the perforation process. FIGS. 19 to 21 only show the distal end portions of shaft 12 and cannula 30, and the perforator 13.

The cannula 30 guides the shaft, which for such minimally invasive applications is usually quite long (in the range of 50 to 100 mm) and as slender as possible, and, furthermore, keeps it substantially dry and free of contamination by tissue components, but it also protects surrounding tissue from undesired interaction with the vibrating shaft. The guiding function of the cannula may be further improved by designing the combination of a shaft 12 to be activated in a mainly longitudinal vibration and a cannula 30 for protecting the shaft, to have a reduced radial clearance in positions in which the longitudinal vibration of the slender shaft includes a node position (anti-node position of undesired radial vibration). For achieving this improved guiding function, the cannula may include a reduced inner cross section or the shaft an enlarged cross section in the named positions.

The distal edge of the cannula 30 may be a sharp and/or serrated edge or may include pin-shaped protrusions for rendering the cannula 30 suitable for being secured in the repair site by lightly embedding this distal edge in tissue.

Furthermore, the cannula may be equipped with fluid conducts for supplying the repair site with fluid (e.g., saline solution for rinsing the repair site) and/or for removing fluid from the repair site (e.g. saline solution or surplus blood, and, as mentioned further above, possibly bone debris).

According to FIG. 19, the instrument including a shaft 12 and one perforator 13 or a plurality thereof protrudes from the distal cannula end for the perforation process and before and/or after the perforation process may be retracted such that the perforator 13 is protected inside the distal end portion of the cannula 30 (retracted position illustrated in broken lines).

FIG. 20B shows in an axial section a distal part of shaft 12 within a cannula 30 (e.g., an arthroscopic tube). The instrument can be moved in a distal direction relative to the channel. Within cannula 30 is a lumen being for example a lumen as used for optical instruments (camera) used within an arthroscopy. At the distal end of the instrument a perforator 13 is comprised. The instrument is equipped with at least one portion 18 of a larger cross section in the node position N ($\lambda/4$). This larger cross section may be caused by a ring around the instrument wall. This ring may be a polymeric ring or a ring made of the same material as the instrument. The portion 18 may also be rather at set spots. There may be three or four spots within the circumference of the instrument.

Alternatively, or in addition, cannula 30 may include at least one portion 19 of a larger cross section in the node position N ($\lambda/4$). The larger cross section may be built by a bulge of the wall of the cannula. The bulge may be an integral part of the cannula wall and can be formed as a ring having a square cross section. Alternatively, there may be several rectangles sitting on one cycle around the sonotrode with some space between them. These rectangles can be arranged within a consistent interval on that circle. Instead of rectangles there may also be spherical bulges attached on one circle around the sonotrode. The circle is always located in a node position N. This embodiment is illustrated in the cross-sections of the cannula 30 shown in FIG. 20A. As can be seen, three or four rectangle bulges causes a larger cross section of the channel. Between these bulges is free space, which may serve as space for a liquid (cooling/flushing). At the distal end of cannula 30 may be attached a polymeric bushing 31 which is able to lower frictional loss. The bushing may be made of a polymer such as PEEK and is attached to the inner surface of cannula 30. Alternatively, shaft 12 or perforator 13 may have a polymeric rind attached to its distal end.

According to FIG. 21, the shaft 12 has a larger cross section than the perforator 13 and the cannula 30 has a partly closed distal end, its distal opening 31 being reduced to a cross section smaller than the cross section of the shaft 12 and therewith limiting distally oriented axial movement of the instrument in the cannula 30 such limiting a depth to which the perforator 13 can be impacted into a dense bone layer, i.e., limiting the depth of an opening to be created.

Figure 22:
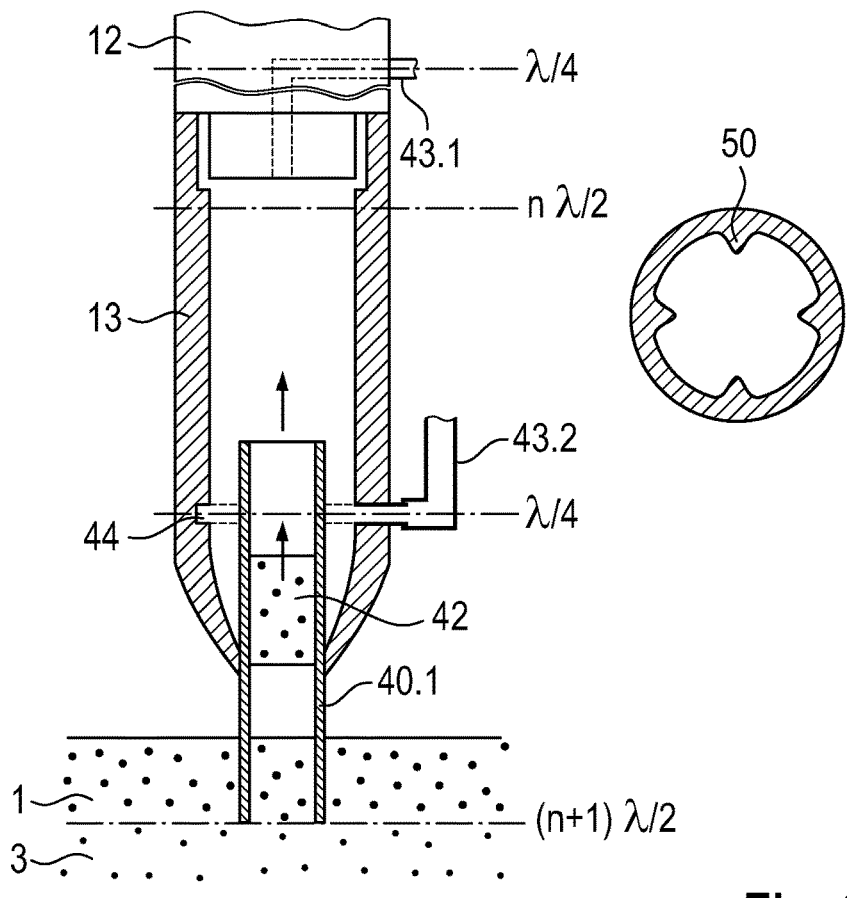
FIG. 22 illustrates another exemplary embodiment of the arrangement of shaft and perforator suitable for the device according to the invention and suitable for removal of the punched bone cone from the operations side.

FIG. 22 shows an embodiment of the arrangement of shaft 12 and perforator 13 similar to the one of FIGS. 18 and 19 being suitable for creating a series of bone openings before being removed from the operation site, and for removal of bone tissue (in particular the complete bone fragments punched out) from the openings created using the instrument. For this purpose, the hollow perforator 13 comprises, in its distal end portion, a cutting tube 40.1. This cutting tube may end in an opening of the perforator having a larger cross section than the cutting tube and being suitable for storage of bone fragments 42. The perforator 13 may be designed for single use, suitable to create several bone openings within one operation side and store the resulting (stamped or punched out) bone fragments.

The embodiment of FIG. 22 is designed so that vacuum facilitates transport of the bone fragments 42 through the cutting tube 40.1 and retains them within the perforator. Therefore, there may be a channel 43.1 within the shaft 12 for pulling out air and applying vacuum within the perforator. This channel 43.1 may be created to run along the longitudinal axis of shaft 12. The channel may leave the shaft 12 lateral. This means the proximal part of the channel 43.1 runs perpendicular to the longitudinal axis and the distal part of the channel. Alternatively, a channel 43.2 may be attached to a flange which protrudes from the perforator 13. At the height where the flange protrudes from the perforator a peripheral groove 44 may be located within the perforator wall. This groove extends once around the complete circumference (dotted line). It is preferred that the channel 43.1 or 43.2 is attached to the instrument in a node position ($\lambda/4$). A channel 43.1 comprised within the shaft 12 and perhaps the handle has to be cleaned after each operation (each treatment of a patient). A channel 43.2 integrated in the perforator 13 has the advantage that it has not be cleaned in case the perforator is a disposable item or is easier to clean because it is very short and without bend structure. On the other side it is more expensive to include such a channel in the perforator, in particular in case that it is a disposable item. The vacuum may also be used to supports or facilitates breaking away the portion of the dense bone punched out. Therefore, it is possible to remove the bone within the cutting tube in one piece and without less damage to the surrounding tissue.

As shown in FIG. 22 the cutting tube of a perforator may reach into the space within the perforator, such as a syphon. FIG. 22 shows also a possible cross section of a cutting tube. The cutting tube may have ribs 50 on its inner side. These ribs may run parallel to the longitudinal axis of the cutting tube and along the complete length of the cutting tube or are arranged only in a distal part which lays outside of the perforator opening. The ribs may alternatively form spirals or curves on the inner side of the cutting tube. The ribs or protruding spikes or alternative protruding elements attached to the inner side of the cutting tube may facilitate breaking away of bone fragments after introduction of the cutting tube into the dense bone. Therefore the cutting tube or the complete instrument has to be rotated, so that torsion is applied to the bone fragment within the cutting tube. These cutting tubes may be made by extrusion or additive manufacturing processes.

Figure 23:
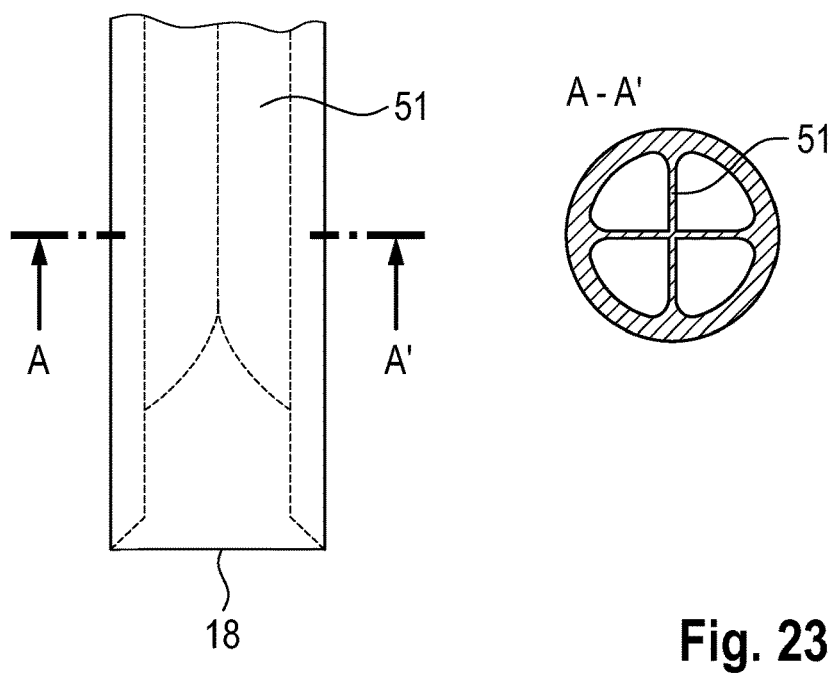
FIG. 23 illustrates an exemplary embodiment of a perforator suitable for the device according to the invention, in an axial section and a cross-section.

FIG. 23 illustrates another embodiment of a cutting tube or perforator. Slicing elements 51 are arranged within the tube or perforator. These elements are suitable for cutting or breaking the bone core into small fragments respectively bone debris which may be aspirate from the perforator. The slicing elements may be formed as thin blades (e.g. two, three, four or five blades) which are arranged in a way to meet one another at the central axis of the tube as illustrated in the cross section of FIG. 23. The cutting tube may cut into the dense bone with its distal end and when cutting deeper into the bone the slicing elements chop the bone core into smaller fragments. The distal ends of the slicing elements or blades may be sharp and may be slanting.

Figure 24A:
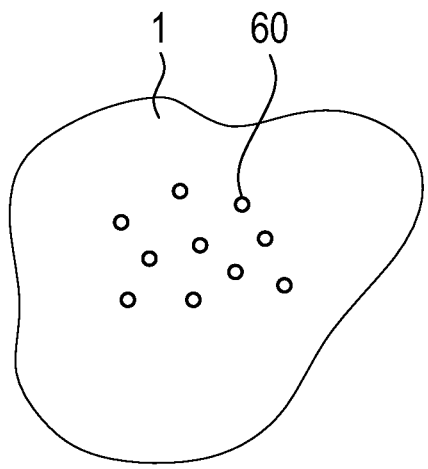
FIG. 24A-24B illustrates two alternative approaches for perforation of a dense bone layer using a device according to the invention.
Figure 24B:
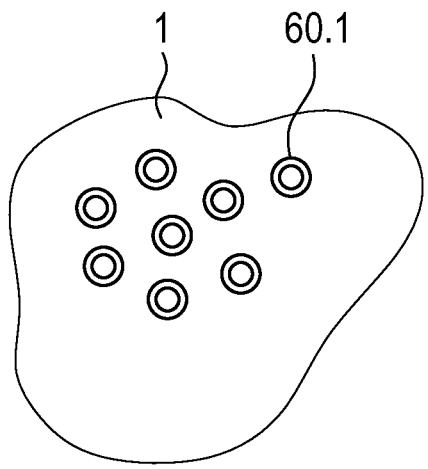

FIGS. 24A-24B show two different methods of perforating a dense bone layer 1 with the aim of enabling transport of blood, viable cells and/or oxygen from an inner side of the dense bone layer to an opposite outer side of the dense bone layer using a device according to the invention. In FIG. 24A the used device introduces several micro holes. The holes can have different cross sections, e.g., rectangular, oval or irregular. The cross section is preferably round and may have a diameter between 1 and 2 mm. The perforator used within this method may have a solid distal end and pushes the dense bone material into the trabecular part of the bone which is compacted thereby. Alternatively, as shown in FIG. 24B, the device used includes a hollow perforator or at least a hollow cutting tube of the perforator and the bone cone is not eliminated. FIG. 24B illustrates the result of a method of perforating a dense bone layer with the aim of enabling transport of blood, viable cells and/or oxygen from an inner side of the dense bone layer to an opposite outer side of the dense bone layer, the method comprising:

providing a device according to the invention, the device including a vibration generator, a shaft defining a principal shaft axis and a distal end piece with a hollow, substantially cylindrical perforator defining a principal perforator axis, positioning the device such that the principal perforator axis is oriented substantially perpendicular, relative to the dense bone layer and a distal end of the perforator is positioned against the dense bone layer, activating the vibration generator and holding the perforator against the dense bone layer for a time sufficient to create a substantially cylindrical opening through or at least into the dense bone layer, and removing the perforator from the opening, whereby the cross section of the substantially cylindrical opening is substantially ring-shaped. This means that a bone core is left within the substantially cylindrical opening. This bone structure has contact to the underlying trabecular bone and optionally also to deeper parts of the dense bone but there is a cut with a closed geometry within the dense bone and with bone structure in the middle having the complete (original) thickness of the treated bone. The ring-shaped cross section of the cylindrical opening may have a diameter of 0.1 to 0.75 mm, and preferably of 0.25 to 0.5 mm.

To create substantially cylindrical openings with a substantially ring-shaped cross section results in a larger surface for bleeding with the same number of perforations. The circumference of the cylindrical opening is a source of bleeding and also the bone core in the middle. At the same time the bone is not weaker or even less fragile. The devices of the present invention are suitable for this method because the perforator geometry is optimized for minimal heat impact to the bone and to minimize debris formation.

Figure 25A:
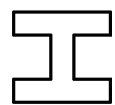
FIG. 25A-25C shows exemplary cross-sections of shafts suitable for a device according to the invention and used for stiffening of a long shaft.
Figure 25B:
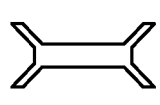
Figure 25C:
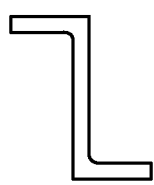

FIGS. 25A-25C show three alternative cross sections of the shaft which are suitable to increase stiffness of the shaft. The shaft may have a cross section in form of a double T, Z or X of course the cross section may also be oval, round or rectangular. Also an instrument having a shaft not being round may be adapted to fit to a round or oval perforator. This may be done by a respective design of the proximal end of the perforator or the distal end of the shaft. Alternatively, there may be an adaptor between both elements transmitting vibration from the shaft to the perforator.

Figure 26A:
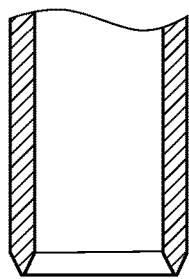
FIG. 26A-26E shows exemplary distal ends of a perforator suitable for a device according to the invention.
Figure 26B:
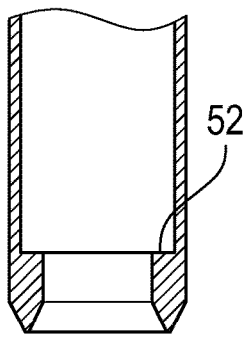

FIGS. 26A and 26B show alternative arrangements of the distal end of a perforator suitable for a device according to the invention. In FIG. 26A the hollow distal end of the perforator or the cutting tube may be sharpened to create peaks or tips. Such peaks may enhance the piercing capacity of the penetrator according to the invention. The peak should preferably be located in a way that it is the first structure to penetrate the bone. The peak may, therefore, be located at the outer, the inner edge or in the middle of the perforator wall. Alternatively, the distal end portion of the perforator may be formed to have different facets. Each facet is a small plane surface at the distal edge. Thus, three or more peaks may result at the distal end, where different facets hit each other.

FIG. 26B shows also a sharp distal end of the perforator or respectively the cutting tube comprised by the perforator. The distal end of the perforator or its cutting tube shows a groove 52, which bounds a sharp, distal cutting edge. The groove consists of a groove 16 which runs on the inner side of the perforator or its cutting tube and runs parallel to the distal cutting edge. The wall of the perforator within the groove 52 is thinner as the wall of the distal cutting edge. The wall within the groove may be between 0.05 and 0.5 mm lower than the edge. The minimal depth of the groove is sufficient to adequately lower the friction. It is preferred that the wall of the perforator or respectively its cutting tube increases abruptly or gradually towards the proximal end. Alternatively, the distal cutting edge has a thicker wall than the remaining cutting tube or perforator. In this case 52 refers to a step and not a groove. Thus, the distal end of the perforator or its cutting tube may include a step 52, where the wall thickness increases in a way that distal of the step the wall is thicker than proximal of the step. The groove or respectively step 52 may also be located on the outer side of the perforator or its cutting tube.

Figure 26C:
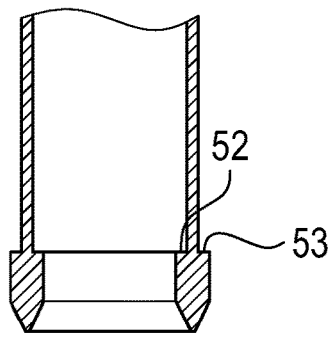

The distal end illustrated in FIG. 26C is similar to the one of FIG. 26B, but there is a groove 52 on the inner side of the distal end of the perforator or its cutting tube and another groove 53 on the outer side. Again 52 and or 53 may also refer to a step within the wall of the perforator or its cutting tube. Steps 52 and 53 may also be designed to form a curvature.

Figure 26D:
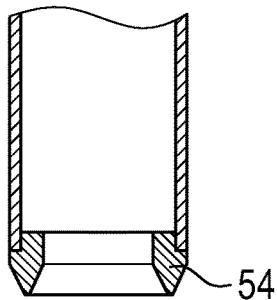

In the embodiment illustrated in FIG. 26D, the distal cutting edge of the perforator or its cutting tube are formed by a ring 54 inserted or pressed in the distal end of the perforator or its cutting edge. The ring may be made of a material different from the perforator or its cutting tube. The ring may be made of metal, an alloy or a ceramic or any material hart enough to cut bone. The ring may be designed to form a sharp distal edge.

Figure 26E:
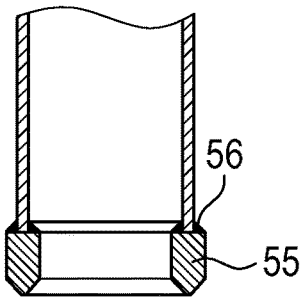

Similar to the ring 54 in FIGS. 26D-26E show a ring or part of a ring 55 put on the distal end of the perforator or its cutting tube and being welded (by laser or ultrasound) to the wall of the perforator or its cutting tube. The material 56 remaining after welding sits on the proximal end of the ring 55. The ring 55 may form a sharp cutting edge for introducing into the bone, wherein the wall of the perforator or its cutting tube may be thinner. The minimal thickness of the wall is sufficient to adequately lower the friction.

Figure 27A:
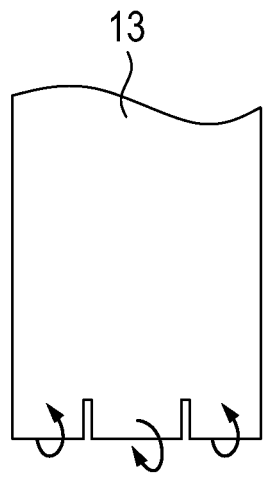
FIG. 27A-27D illustrates another variation of the distal end of a perforator suitable for a device according to the invention.
Figure 27B:
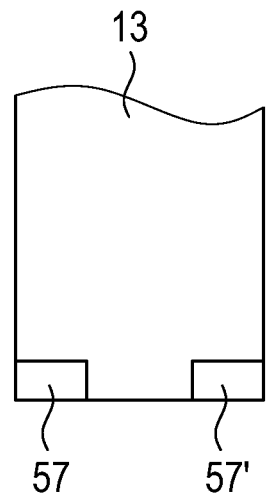
Figure 27C:
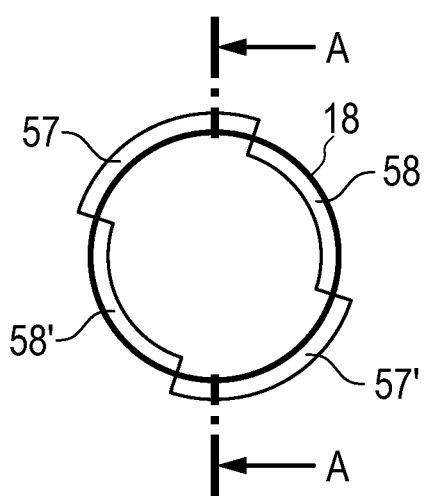
Figure 27D:
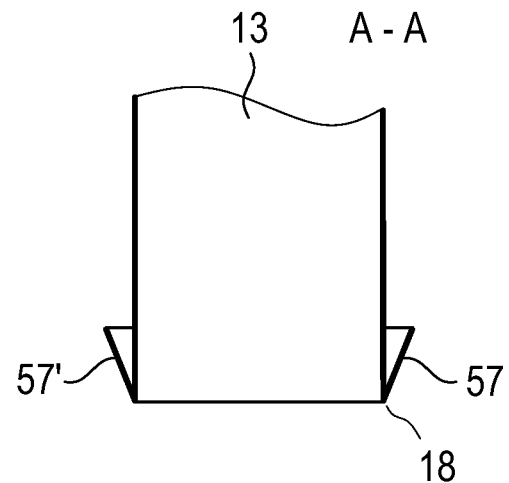

FIGS. 27A-27D show another embodiment of an arrangement of the distal end of a perforator or its cutting tube suitable for a device according to the invention. The distal end is alternatingly folded. Therefore, the tubular distal end has at least two incisions. The parts between the incisions are alternating folded inwards or outwards. FIG. 27A illustrates the distal end with incisions before folding. FIG. 27B shows parts 57 and 57' being folded outwards, wherein the part in-between has been folded inwards. FIG. 27C shows a cross section of the folded distal end having 4 incisions and parts 57, 57' being folded outwards and parts 58 and 58' being folded inwards. The fold should be in a way that a sharp cutting edge 18 results, as illustrated in FIG. 27D being a cut at A to A'.

Figure 28:
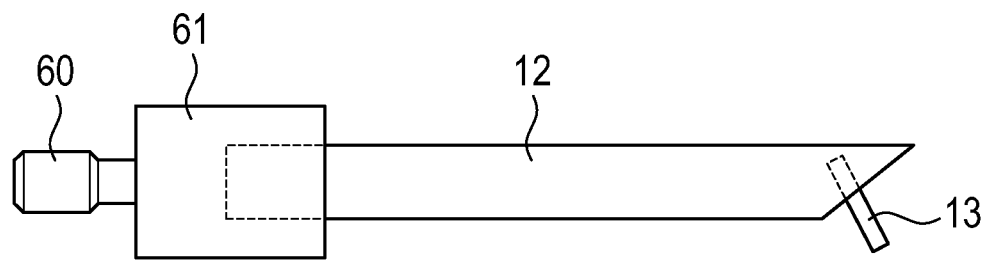
FIG. 28 illustrate an exemplary embodiments of the instrument suitable for a device according to the invention.

FIG. 28 shows an instrument according to the invention including a shaft 12 and one perforator 13. The perforator has been pressed in the shaft 12 (illustrated in broken lines) and laser welded to be secured. The perforator may be a hollow tube with a length of 10 to 14 mm, an outer cross section of 1 to 1.4 mm and an inner cross section of 0.6 to 1 mm. the length of the perforator part being outside the shaft is about 7 mm. The outer diameter of the cross section of the shaft may be 3 to 5 mm. The shaft has been press fit into a base 61 having a proximal element 60 (thread or plug-in) for connection to the handle and/or the vibration generator.

Figure 29:
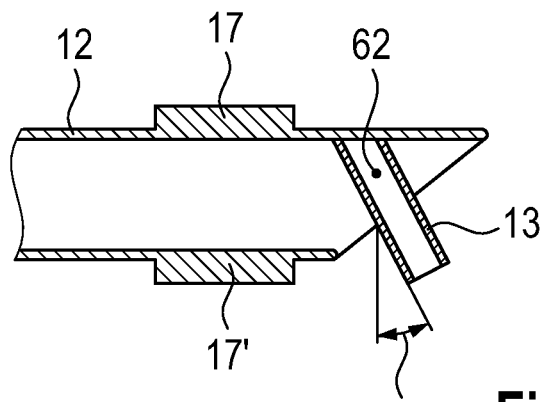
FIG. 29 illustrates another exemplary embodiment of the arrangement of shaft and perforator suitable for the device according to the invention.

FIG. 29 illustrates an embodiment of the arrangement of shaft 12 and hollow perforator 13, similar to FIG. 28. The angle α as well as the mass of element 17 influence the axial amplitude of the vibration. The mass of element 17 may be chosen in a way that the maximal amplitude is at point 62. In case that the angle α is nearly 0° position 62 is at λ/4. Element 17 may be a ring-shaped increase of the wall thickness. Alternatively, it may consists of at least two solid objects 17 and 17' attached symmetrically to shaft 12.

Figure 30:
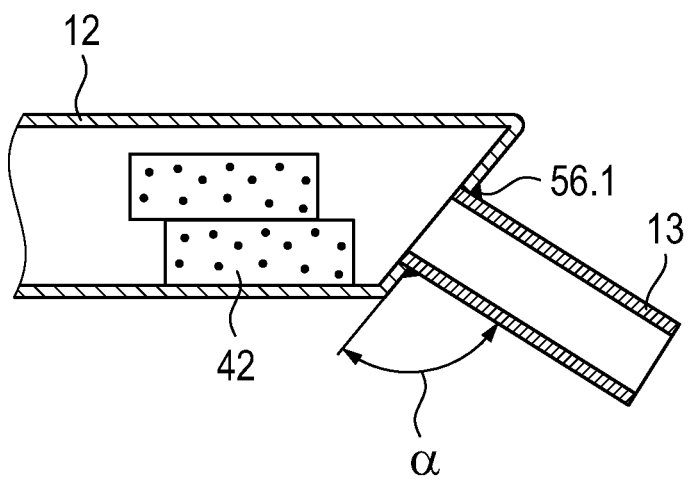
FIG. 30 illustrates another exemplary embodiment of the arrangement of shaft and perforator suitable for the device according to the invention.

FIG. 30 illustrates an embodiment of the arrangement of shaft 12 and hollow perforator 13, similar to FIG. 28. The shaft 12 is a hollow tube with an oblique-cut distal end. The distal end may be closed by a plate which may be welded to the tube. The hollow perforator (having the form of a tube) can be pressed into said plate and welded to the plate (cf. remains 56.1). The plate can serve as a depth limiting element. The outer diameter of the perforator may between 6 and 10 mm. The angle α may be >90° and <180° and is preferably between 120° and 150°. The geometry of the shaft 12 can have anyone as described herein, e.g. there may be space for storage of bone fragments 42. There may be a supply for a cooling liquid from the handle to the inner pace of the shaft 12 (not shown). In addition the distal end of the perforator may be designed as shown in FIGS. 26 A to E and FIG. 27.

Analogous to the arrangements of shaft 12 and hollow perforator 13 shown in FIGS. 29 and 30 also a cutting tube 40 may be attached oblique to a perforator 13.

What is claimed is:

1. A device for perforating a dense bone layer, the device comprising a vibration generator for generating mechanical vibration and an instrument with a shaft and a distal end piece comprising a perforator, wherein the shaft has a distal end, a proximal end and a principal longitudinal shaft axis extending between the proximal end and the distal end, wherein the distal end piece is arranged at the distal end of the shaft and the proximal end of the shaft is connected or connectable to the vibration generator, wherein the perforator comprises a solid or a hollow cylinder or prism defining a principal perforator axis, and wherein the vibration generator, the shaft and the distal end piece are adapted to each other for the shaft to transmit mechanical vibration from the vibration generator to the distal end piece and for vibrating the perforator in a direction parallel to the principal perforator axis, wherein the principal perforator axis is angled relative to the principal longitudinal shaft axis,
   wherein the shaft comprises an element, wherein said element provides a ring-shaped increase of wall thickness or comprising two solid objects attached symmetrically to the shaft, said element having a mass, the mass of the element influencing an axial amplitude of the mechanical vibration.

2. The device according to claim 1, wherein the axis and the distal end piece with the perforator are made as one piece or are rigidly coupled to each other for forming one vibrating element together.

3. The device according to claim 1, wherein the perforator comprises a cutting tube.

4. The device according to claim 1, wherein the perforator or the shaft comprises an opening suitable for storage of removed bone fragments.

5. The device according to claim 4, wherein the shaft or the perforator comprises a pipeline suitable for liquid supply to the opening or applying vacuum to the opening.

6. The device according to claim 1, wherein the principal shaft axis and the principal perforator axis form an angle that is >90° and <180°.

7. The device according to claim 6, wherein the shaft is designed to vibrate in a mainly transversal or bending mode, or wherein the shaft is designed to vibrate in a mainly longitudinal mode and the distal end piece with the perforator is designed for deflecting the longitudinal shaft vibrating to a longitudinal vibration in the direction of the principal perforator axis.

8. The device according to claim 1, wherein the perforator is a solid cylinder and comprises a concave distal face with a distal outer edge.

9. The device according to claim 1, wherein the perforator or its cutting tube is a hollow cylinder and comprises a distal edge.

10. The device according to claim 9, wherein the distal edge terminates an inner and/or outer tapering of a cylinder wall.

11. The device according to claim 10, wherein the distal edge comprises a groove.

12. The device according to claim 9, wherein the distal edge comprises a ring clamped into the opening of the hollow perforator or the hollow cutting tube.

13. The device according to claim 9, wherein the distal edge is sharp or serrated, the serration having a size in the visible or sub-visible range.

14. The device according to claim 1, wherein a distal end of the shaft or the perforator comprises a depth limiting element.

15. The device according to claim 1 and further comprising a cannula, wherein the shaft extends in a longitudinal channel of the cannula.

16. The device according to claim 15, wherein a distal edge of the cannula is a sharp or serrated edge or comprises pin-shaped protrusions extending therefrom.

17. The device according to claim 15, wherein the distal end piece with the perforator is retractable into a distal end of the cannula.

18. The device according to claim 15, wherein the instrument and/or the cannula comprises at least one portion of a larger cross section.

19. The device according to claim 15, wherein the cannula further comprises at least one conduit for transport of a fluid to the repair site and/or away from the repair site.

20. The device according to claim 1, wherein the perforator or the cutting tube comprises protruding elements, such as ribs, on the inner surface suitable to exert torsion force to the cut bone.

21. A device for perforating a dense bone layer, the device comprising a vibration generator for generating mechanical vibration and an instrument with a shaft and a distal end piece comprising a perforator, wherein the shaft has a distal end, a proximal end and a principal longitudinal shaft axis extending between the proximal end and the distal end, wherein the distal end piece is arranged at the distal end of the shaft and the proximal end of the shaft is connected or connectable to the vibration generator, wherein the perforator comprises a solid or a hollow cylinder or prism defining a principal perforator axis, and wherein the vibration generator, the shaft and the distal end piece are adapted to each other for the shaft to transmit mechanical vibration from the vibration generator to the distal end piece and for vibrating the perforator in a direction parallel to the principal perforator axis,
wherein the perforator or its cutting tube is a hollow cylinder and comprises a distal edge, and
wherein the distal edge is formed by a ring welded to the perforator or the cutting tube.

22. A device for perforating a dense bone layer, the device comprising a vibration generator for generating mechanical vibration and an instrument with a shaft and a distal end piece comprising a perforator, wherein the shaft has a distal end, a proximal end and a principal longitudinal shaft axis extending between the proximal end and the distal end, wherein the distal end piece is arranged at the distal end of the shaft and the proximal end of the shaft is connected or connectable to the vibration generator, wherein the perforator comprises a solid or a hollow cylinder or prism defining a principal perforator axis, and wherein the vibration generator, the shaft and the distal end piece are adapted to each other for the shaft to transmit mechanical vibration from the vibration generator to the distal end piece and for vibrating the perforator in a direction parallel to the principal perforator axis,
wherein the perforator or its cutting tube is a hollow cylinder and comprises a distal edge, and
wherein the distal edge is formed by parts of the perforator of the cutting tube being folded alternatingly outwards and inwards.

23. A device for perforating a dense bone layer, the device comprising a vibration generator for generating mechanical vibration and an instrument with a shaft and a distal end piece comprising a perforator, wherein the shaft has a distal end, a proximal end and a principal longitudinal shaft axis extending between the proximal end and the distal end, wherein the distal end piece is arranged at the distal end of the shaft and the proximal end of the shaft is connected or connectable to the vibration generator, wherein the perforator comprises a solid or a hollow cylinder or prism defining a principal perforator axis, and wherein the vibration generator, the shaft and the distal end piece are adapted to each other for the shaft to transmit mechanical vibration from the vibration generator to the distal end piece and for vibrating the perforator in a direction parallel to the principal perforator axis,
wherein the perforator or the cutting tube comprises slicing elements, within the inner space suitable to chop bone.

24. An instrument that is a component of a device for perforating a dense bone layer, wherein the device includes a vibration generator for generating mechanical vibration, the instrument comprising a shaft and a distal end piece comprising a perforator, wherein the shaft has a distal end, a proximal end and a principal longitudinal shaft axis extending between the proximal end and the distal end, wherein the distal end piece is arranged at the distal end of the shaft and the proximal end of the shaft is designed to be connected to a vibration generator, wherein the perforator comprises a solid or a hollow cylinder or prism defining a principal perforator axis, and wherein the shaft and the distal end piece are adapted to each other for the shaft to transmit mechanical vibration from the proximal end of the shaft to the distal end piece and for vibrating the perforator in a direction parallel to the principal perforator axis, wherein the principal perforator axis is angled relative to the principal longitudinal shaft axis, and
wherein the shaft comprises an element, wherein said element provides a ring-shaped increase of wall thickness or comprising two solid objects attached symmetrically to the shaft, said element having a mass, the mass of the element influencing an axial amplitude of the mechanical vibration.

25. The instrument according to claim 24 and further comprising a cannula.

26. A method of perforating a dense bone layer with the aim of enabling transport of blood, viable cells and/or oxygen from an inner side of the dense bone layer to an opposite outer side of the dense bone layer, the method comprising the steps of:
providing a device according to claim 1, the device comprising a vibration generator, a shaft defining a principal shaft axis and a distal end piece with a solid or hollow, substantially cylindrical perforator defining a principal perforator axis,
positioning the device such that the principal perforator axis is oriented non-parallel, preferably substantially perpendicular, relative to the dense bone layer and a distal end of the perforator is positioned against the dense bone layer,
activating the vibration generator and holding the perforator against the dense bone layer for a time sufficient to create a substantially cylindrical opening through or at least into the dense bone layer, and removing the perforator from the opening.

27. The method according to claim 26, wherein said method is performed in open surgery or in minimally invasive surgery.

28. The method according to claim 26, wherein the dense bone layer is a subchondral bone plate of a joint of a human or animal patient or a cortical bone plate of a body of a vertebra of a human or animal patient.

* * * * *